US012731262B2

(12) United States Patent
Xue et al.

(10) Patent No.: US 12,731,262 B2
(45) Date of Patent: Sep. 8, 2026

(54) SEGMENTATION MODEL LEARNING METHOD, PROCESSING CIRCUITRY, COMPUTER PROGRAM PRODUCT, AND MEDICAL INFORMATION PROCESSING DEVICE

(71) Applicant: Canon Kabushiki Kaisha, Tokyo (JP)

(72) Inventors: Xiao Xue, Beijing (CN); Gengwan Li, Beijing (CN); Bing Han, Beijing (CN)

(73) Assignee: Canon Kabushiki Kaisha, Tokyo (JP)

( * ) Notice: Subject to any disclaimer, the term of this patent is extended or adjusted under 35 U.S.C. 154(b) by 327 days.

(21) Appl. No.: 18/599,801

(22) Filed: Mar. 8, 2024

(65) Prior Publication Data

US 2024/0303821 A1 Sep. 12, 2024

(30) Foreign Application Priority Data

Mar. 8, 2023 (CN) ........................ 202310224271.4

(51) Int. Cl.
*G06T 7/11* (2017.01)
*G06T 7/00* (2017.01)
(Continued)

(52) U.S. Cl.
CPC .............. *G06T 7/11* (2017.01); *G06T 7/0012* (2013.01); *G16H 30/20* (2018.01); *G16H 30/40* (2018.01);
(Continued)

(58) Field of Classification Search
CPC ..................... G06T 7/11; G06T 7/0012; G06T 2207/20081; G06T 2207/30056;
(Continued)

(56) References Cited

U.S. PATENT DOCUMENTS 11,562,585 B2 1/2023 Courtiol et al.
2021/0271847 A1 9/2021 Courtiol et al.
(Continued)

FOREIGN PATENT DOCUMENTS

CN 109584252 B 8/2020
JP 2022-538866 A 9/2022

OTHER PUBLICATIONS

Stoecker et al., "Determination of Lung Segments in Computed Tomography Images Using the Euclidean Distance to the Pulmonary Artery", Medical Physics, vol. 40, No. 9, Sep. 2013, 11 pages.

*Primary Examiner* — Mekonen T Bekele
(74) *Attorney, Agent, or Firm* — Oblon, McClelland, Maier & Neustadt, L.L.P.

(57) ABSTRACT

A segmentation model learning method according to an embodiment includes learning that, based on a loss function value, includes performing supervised learning of the voxels in medical image data according to the region to which the voxels belong. The learning of the medical image data includes: using first-type labeling information, which is meant for segmenting a predetermined structure into a plurality of categories, about the voxels of a predetermined structure and causing a segmentation model to perform direct supervised learning that represents learning for segmentation of the predetermined structure into a plurality of categories; using second-type labeling information, which is meant for segmenting a massive region covering the predetermined structure into a plurality of blocks, about the voxels of a massive region and causing the segmentation model to perform indirect supervised learning that represents learning for segmentation of the massive region into a plurality of categories; and optimizing the network parameters of the segmentation model.

10 Claims, 9 Drawing Sheets

(51) Int. Cl.
*G16H 30/20* (2018.01)
*G16H 30/40* (2018.01)

(52) U.S. Cl.
CPC ............... *G06T 2207/20081* (2013.01); *G06T 2207/30056* (2013.01); *G06T 2207/30061* (2013.01); *G06T 2207/30101* (2013.01)

(58) Field of Classification Search
CPC ........... G06T 2207/30061; G06T 2207/30101; G16H 30/20; G16H 30/40; G06N 3/08
See application file for complete search history.

(56) References Cited

U.S. PATENT DOCUMENTS

| | | | | |
|---|---|---|---|---|
| 2021/0338330 | A1* | 11/2021 | Rao | A61B 34/10 |
| 2023/0343063 | A1* | 10/2023 | Xu | G06T 7/194 |
| 2023/0386024 | A1 | 11/2023 | Courtiol et al. | |

* cited by examiner

FIG.2
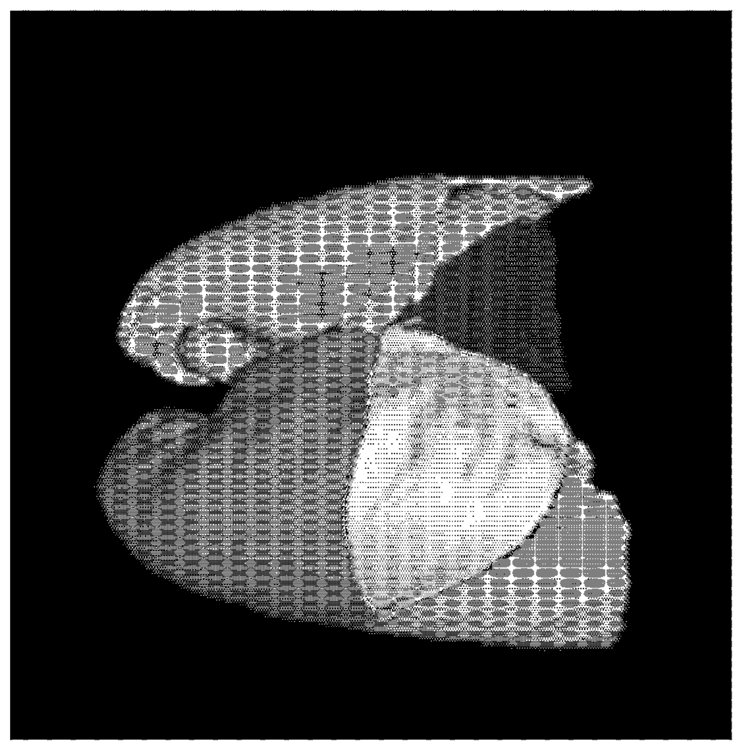
SECOND-TYPE LABELING INFORMATION
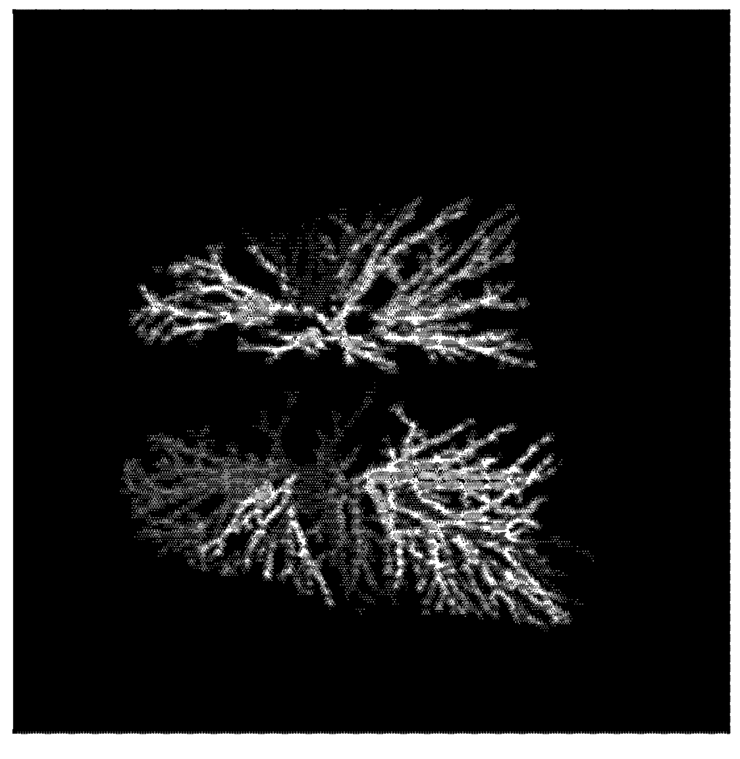
FIRST-TYPE LABELING INFORMATION

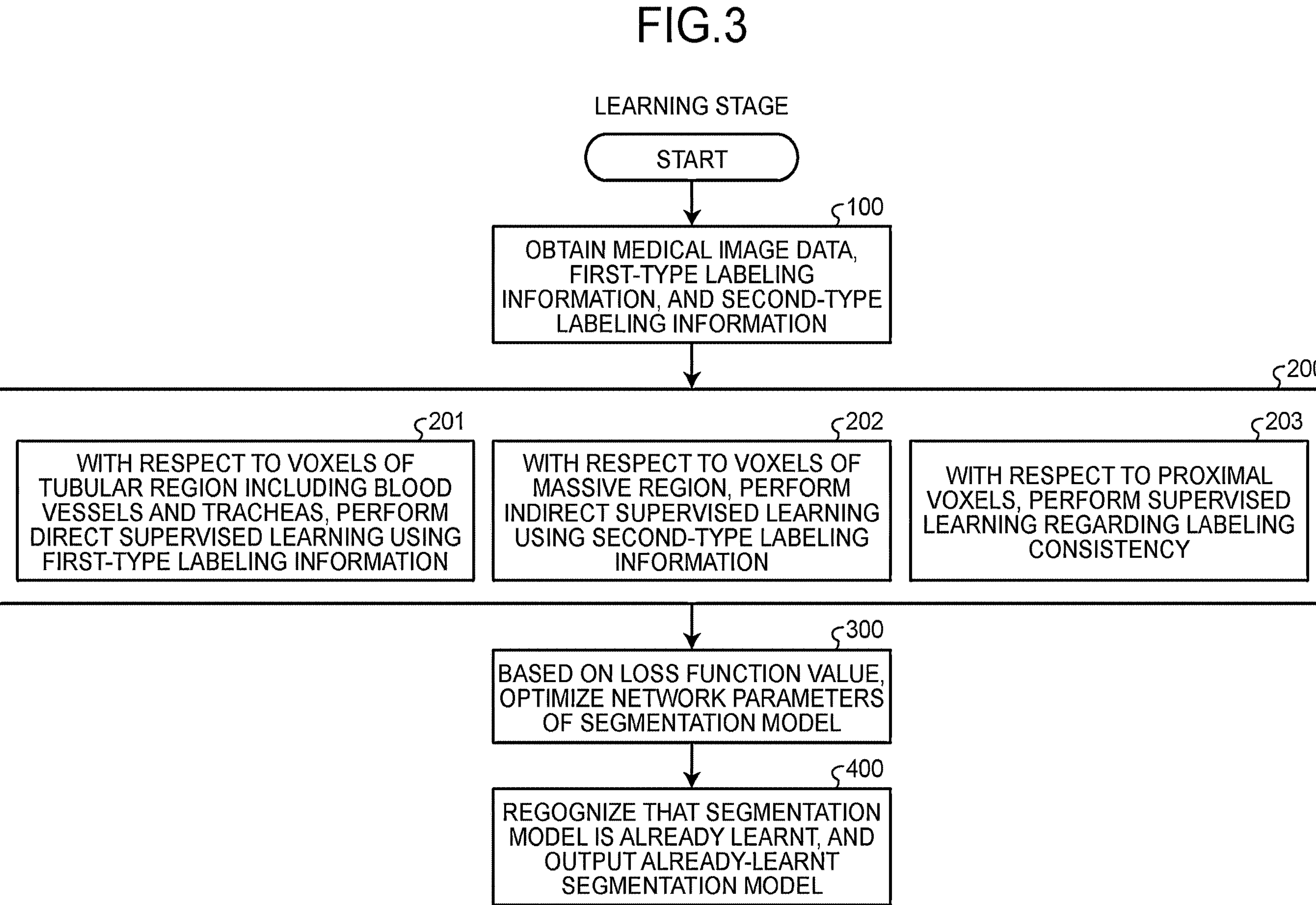
FIG.3
LEARNING STAGE
START
100
OBTAIN MEDICAL IMAGE DATA, FIRST-TYPE LABELING INFORMATION, AND SECOND-TYPE LABELING INFORMATION
200
201
WITH RESPECT TO VOXELS OF TUBULAR REGION INCLUDING BLOOD VESSELS AND TRACHEAS, PERFORM DIRECT SUPERVISED LEARNING USING FIRST-TYPE LABELING INFORMATION
202
WITH RESPECT TO VOXELS OF MASSIVE REGION, PERFORM INDIRECT SUPERVISED LEARNING USING SECOND-TYPE LABELING INFORMATION
203
WITH RESPECT TO PROXIMAL VOXELS, PERFORM SUPERVISED LEARNING REGARDING LABELING CONSISTENCY
300
BASED ON LOSS FUNCTION VALUE, OPTIMIZE NETWORK PARAMETERS OF SEGMENTATION MODEL
400
REGOGNIZE THAT SEGMENTATION MODEL IS ALREADY LEARNT, AND OUTPUT ALREADY-LEARNT SEGMENTATION MODEL

FIG.5

FIG.8
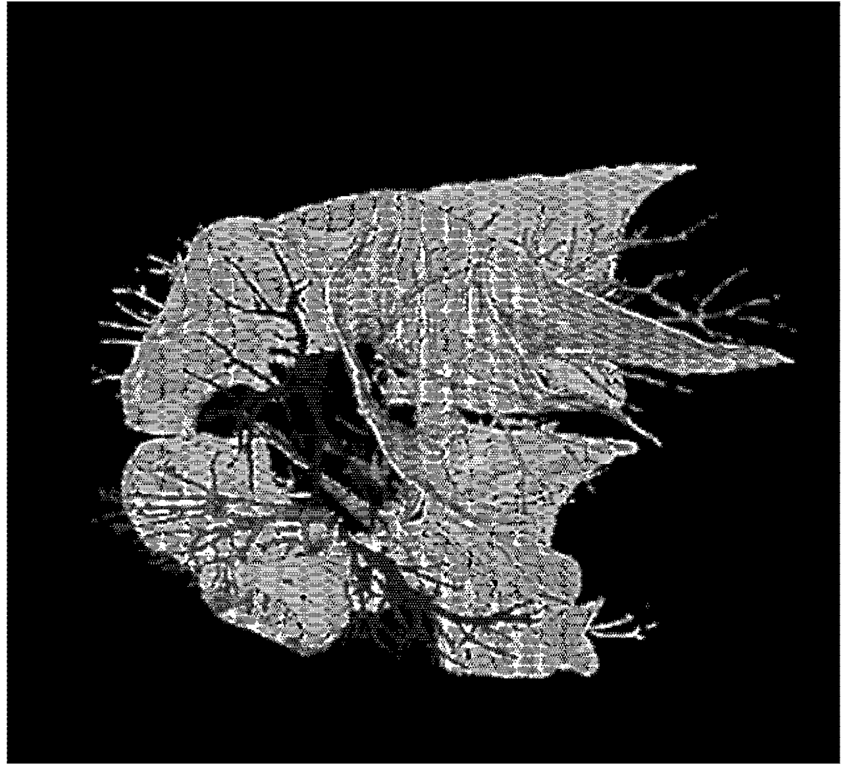
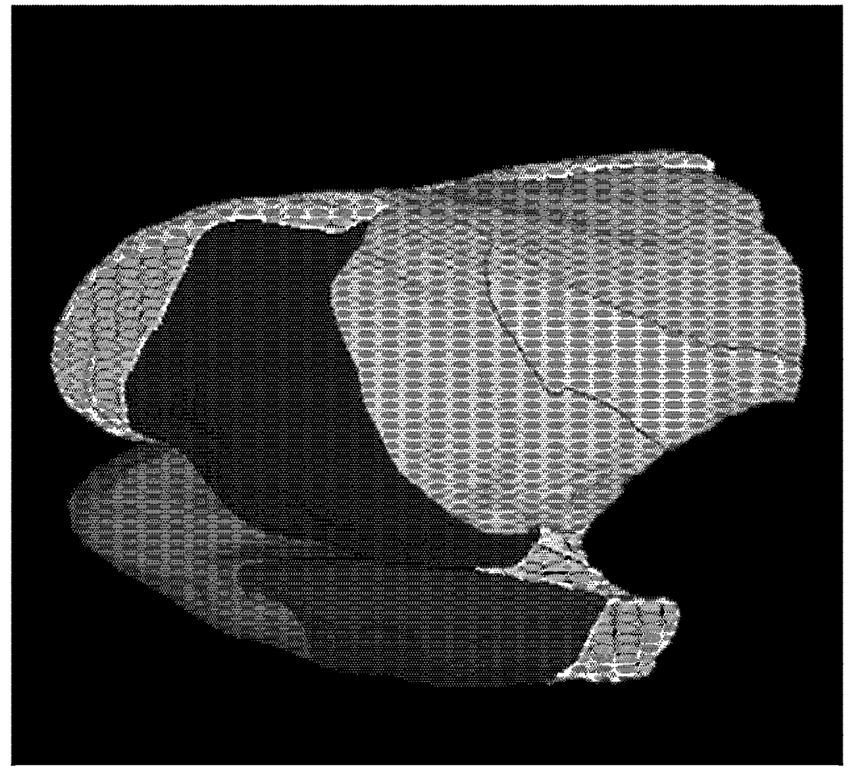

SEGMENTATION MODEL LEARNING METHOD, PROCESSING CIRCUITRY, COMPUTER PROGRAM PRODUCT, AND MEDICAL INFORMATION PROCESSING DEVICE

CROSS-REFERENCE TO RELATED APPLICATIONS

This application is based upon and claims the benefit of priority from Chinese Patent Application No. 202310224271.4, filed on Mar. 8, 2023, the entire contents of all of which are incorporated herein by reference.

FIELD

Embodiments described herein relate generally to a segmentation model learning method, processing circuitry, a computer program product, and a medical information processing device.

BACKGROUND

In the diagnosis of disease, identifying the location of the focus of disease is known to be a crucial step in developing a treatment plan. With reference to the lungs as an example, segmentation of the pulmonary lobes and the pulmonary segments represents the first step in identifying the position of the focus of disease.

In that regard, in the conventional technology, a method has been proposed in which, firstly, feature regions such as blood vessels or tracheas assigned with pulmonary segment labeling are generated; pulmonary segment labeling for the other regions is performed based on the distance from the voxels to the feature regions such as the blood vessels or the tracheas; and accordingly total pulmonary segment labeling is generated. However, segmentation generated according to this method generally results in serrated boundaries, and the display result is not favorable for observation to be done by doctors.

Moreover, in the conventional technology, a method is also proposed in which total pulmonary segment labeling is provided, and segmentation of pulmonary segments is performed by means of training (learning) of a model such as a neural network using fully supervised learning. However, the structure of the lung region is complex in nature and, as far as segmentation of the pulmonary lobes into pulmonary segments is concerned, there are no explicit physical boundaries. Hence, generally, labelling becomes a difficult and time-consuming task. Moreover, the boundaries labeled by different doctors happen to be significantly different from each other. As a result, there are times when the learning result gets affected.

BRIEF DESCRIPTION OF THE DRAWINGS

FIG. 2 is a diagram illustrating an example of first-type labeling information and second-type labeling information according to the embodiment;

FIG. 3 is a detailed flowchart of the segmentation model learning method according to the embodiment;

FIG. 5 is schematic diagram illustrating the relationship between the probability map generated at Step 100 and a probability map subjected to indirect supervised learning at Step 202;

FIG. 8 is a diagram illustrating the segmentation result obtained as a result of performing segmentation using an already-learnt segmentation model.

DETAILED DESCRIPTION

Figure 1:
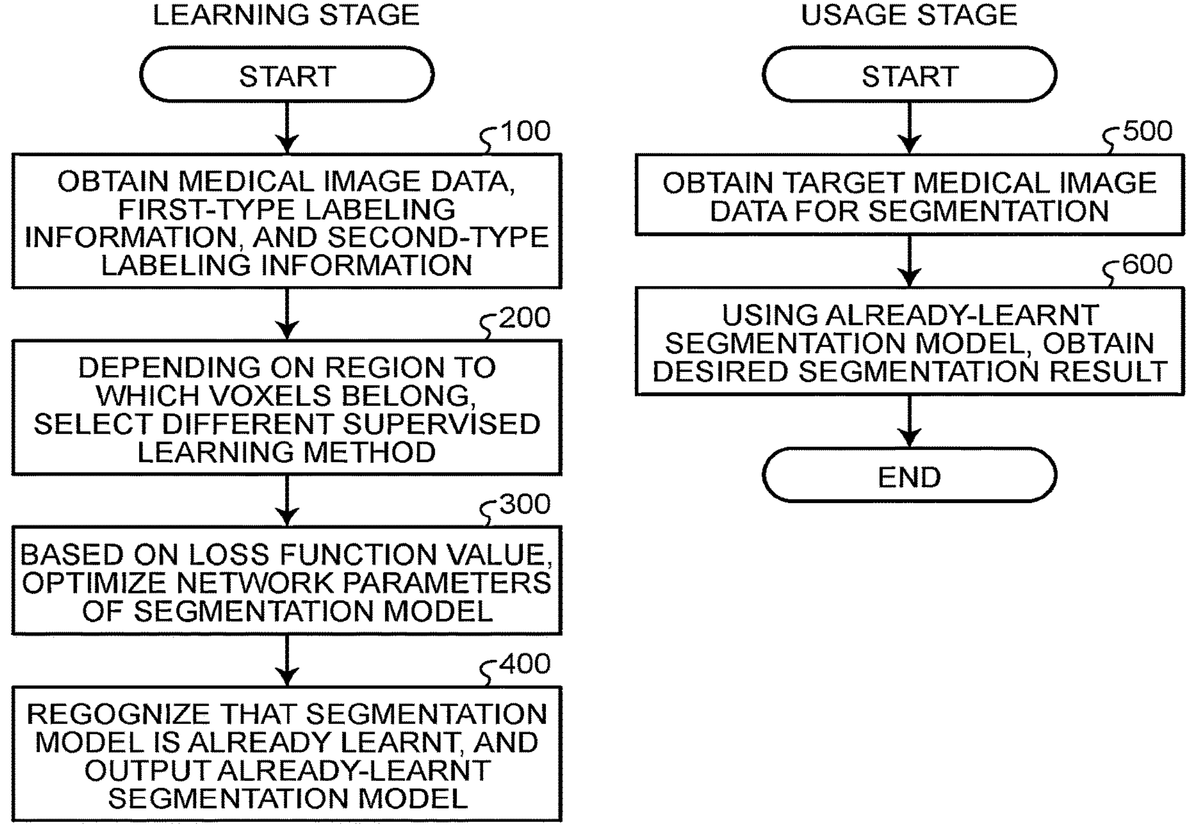
FIG. 1 is a flowchart of the operations performed at the time of learning a segmentation model learning method according to an embodiment, and a usage flowchart of the operations performed at the time of segmentation using the already-learnt segmentation model.

An embodiment described below includes a first technical proposal to an eighth technical proposal.

A segmentation model learning method based on weakly supervised learning according to the first technical proposal includes the following steps: obtaining, as learning data, medical image data, first-type labeling information that is meant for segmenting a predetermined structure into multiple segments (a plurality of categories), and second-type labeling information that is meant for segmenting a massive region, which covers the predetermined structure, into a plurality of blocks; and learning that includes performing, based on a loss function value, supervised learning of voxels in the medical image data according to the regions to which the voxels belong, performing direct supervised learning regarding some of the voxels using the first-type labeling information, performing indirect supervised learning regarding the remaining voxels using the second-type labeling information, and optimizing the network parameters of the segmentation model.

Processing circuitry according to the second technical proposal obtains, as learning data, medical image data, first-type labeling information that is meant for segmenting a predetermined structure into multiple segments, and second-type labeling information that is meant for segmenting a massive region, which covers the predetermined structure, into a plurality of blocks; performs, based on a loss function value, supervised learning of voxels in the medical image data according to the regions to which the voxels belong; performs direct supervised learning regarding some of the voxels using the first-type labeling information; performs indirect supervised learning regarding the remaining voxels using the second-type labeling information; and optimizes the network parameters of the segmentation model.

A computer-readable memory medium according to the third technical proposal is used to store a computer program. The computer program is executed to perform the following operations: obtaining, as learning data, medical image data, first-type labeling information that is meant for segmenting a predetermined structure into multiple segments, and second-type labeling information that is meant for segmenting a massive region, which covers the predetermined structure, into a plurality of blocks; performing, based on a loss function value, supervised learning of voxels in the medical image data according to the regions to which the voxels belong; performing direct supervised learning regarding some of the voxels using the first-type labeling information; performing indirect supervised learning regarding the remaining voxels using the second-type labeling information; and optimizing the network parameters of the segmentation model.

A medical information processing device includes: an obtaining unit that obtains the target medical image data for segmentation which is collected from an examination target, and that obtains an already-learnt segmentation model; a processing unit that segments the target medical image data for segmentation using the already-learnt segmentation model, and obtains the segmentation result regarding segmentation of a predetermined structure and a massive region, which covers the predetermined structure, into multiple segments; and an output unit that outputs the segmentation result. Herein, the already-learnt segmentation model is a segmentation model learnt using the segmentation model learning method according to the first technical proposal.

A segmentation model learning method based on weakly supervised learning according to the fifth technical proposal includes the following steps: obtaining, as learning data, medical image data, first-type labeling information that is meant for segmenting a predetermined structure into a plurality of categories, and second-type labeling information that is meant for segmenting a massive region, which covers the predetermined structure, into a plurality of blocks; and learning that includes performing, based on a loss function value, supervised learning of voxels in the medical image data according to the regions to which the voxels belong. Herein, the learning of the medical image data includes the following steps: using the first-type labeling information about the voxels of the predetermined structure and causing a segmentation model to perform direct supervised learning that represents learning for segmentation of the predetermined structure in the target medical image data for segmentation into a plurality of categories; using the second-type labeling information about the voxels of the massive region and causing the segmentation model to perform indirect supervised learning that represents learning for segmentation of the massive region in the target medical image data for segmentation into a plurality of categories; and optimizing the network parameters of the segmentation model.

Processing circuitry according to the sixth technical proposal obtains, as learning data, medical image data, first-type labeling information that is meant for segmenting a predetermined structure into a plurality of categories, and second-type labeling information that is meant for segmenting a massive region, which covers the predetermined structure, into a plurality of blocks; uses the first-type labeling information about some of the voxels in the medical image data and causes a segmentation model to perform, based on a loss function value, direct supervised learning that represents learning for segmentation of the predetermined structure in the target medical image data for segmentation into a plurality of categories; uses the second-type labeling information about the voxels of the massive region and causes the segmentation model to perform indirect supervised learning that represents learning for segmentation of the massive region in the target medical image data for segmentation into a plurality of categories; and optimizes the network parameters of the segmentation model.

A computer program according to the seventh technical proposal causes a computer to obtain, as learning data, medical image data, first-type labeling information that is meant for segmenting a predetermined structure into a plurality of categories, and second-type labeling information that is meant for segmenting a massive region, which covers the predetermined structure, into a plurality of blocks; and to perform, based on a loss function value, supervised learning of voxels in the medical image data according to the affiliated regions. The supervised learning of the medical image data includes the following steps: using the first-type labeling information about the voxels of the predetermined structure and causing a segmentation model to perform direct supervised learning that represents learning for segmentation of the predetermined structure in the target medical image data for segmentation into a plurality of categories; using the second-type labeling information about the voxels of the massive region and causing the segmentation model to perform indirect supervised learning that represents learning for segmentation of the massive region in the target medical image data for segmentation into a plurality of categories; and optimizing the network parameters of the segmentation model.

A medical information processing device according to the eighth technical proposal includes an obtaining unit that obtains the target medical image data for segmentation which is collected from the examination target, and that obtains an already-learnt segmentation model; a processing unit that segments the target medical image data for segmentation using the already-learnt segmentation model, and obtains the segmentation result indicating segmentation of a predetermined structure and a massive region, which covers the predetermined structure, into multiple segments; and an output unit that outputs the segmentation result. Herein, the already-learnt segmentation model is a segmentation model learnt using the segmentation model learning method according to the fifth technical proposal.

When the segmentation model learning method according to the embodiment is implemented, regarding the voxels of a trachea or a blood vessel, supervised learning is performed using pulmonary segment labeling information. Moreover, regarding each voxel of a pulmonary lobe, from the probability maps of a plurality of categories corresponding to the concerned pulmonary lobe, the maximum numerical value of the voxel is obtained; and supervised learning is performed regarding the maximum numerical value using pulmonary lobe labeling information. Hence, without having to use the total pulmonary segment labeling in the learning process, it becomes possible to enhance the learning efficiency, and to avoid a decline in the accuracy attributed to the difficulty or the differences in the total labeling. Moreover, at the time of performing actual segmentation using an already-learnt segmentation model, it becomes possible to perform segmentation without having to generate pulmonary segment labeling and to obtain comparatively smoother segmentation boundaries.

The embodiment is described below with reference to the accompanying drawings. However, the invention is not limited by the embodiment described below. In the following explanation, the constituent elements having substantially identical functions and configuration are referred to by the same reference numerals, and the explanation is repeated only when necessary. Meanwhile, among the drawings, the same member is sometimes illustrated in a different proportion.

It is known that, based on the supply information (position information) of blood vessels, some structures inside the human body (for example, the lung region and the liver region) can be segmented into substructures indicating multiple segments (a plurality of segments (regions and portions)). As far as the lung region is concerned, generally the lung region includes the left lung and the right lung that are separated into five pulmonary lobes due to the inter-lobe fissures having distinct physical boundaries. The left lung includes two pulmonary lobes, and the right lung includes three pulmonary lobes. Moreover, according to the supply relationship (the positional relationship) of the tracheas and the blood vessels, the five pulmonary lobes can be further segmented into 18 pulmonary segments.

Since the lungs and the pulmonary lobes have distinct physical boundaries with the tracheas and the blood vessels, the level of difficulty of segmentation is not high, and a doctor can perform labelling manually. Moreover, if labeling is performed using a conventional algorithm based on deep learning, then a high degree of labeling accuracy is achieved at a low cost. Hence, labeling can be performed using deep learning. However, the pulmonary lobes, which represent the outer-layer structures in which tracheas and blood vessels are included, do not have distinct physical boundaries on the inside. As a result, it becomes difficult to perform labeling to ensure that the five pulmonary lobes are segmented into 18 pulmonary segments. As explained earlier, when manual labeling (total labeling) is performed from the pulmonary lobes to the pulmonary segments, the labeling is a difficult as well as time-consuming task. Moreover, the boundaries labeled by different doctors happen to be significantly different from each other. As a result, there are times when the learning result gets affected.

In the segmentation model learning method based on weakly supervised learning as proposed in the embodiment, direct supervised learning is performed using the first-type labeling information with respect to the voxels of the tracheas and the blood vessels having pulmonary segment labeling assigned thereto; and indirect supervised learning is performed with respect to the remaining voxels not having pulmonary segment labeling but having pulmonary lobe labeling assigned thereto. Moreover, during the indirect supervised learning, regarding each of the remaining voxels, from the probability maps of a plurality of categories corresponding to the concerned pulmonary lobe, the maximum numerical value of each voxel is obtained, and supervised learning is performed regarding the maximum numerical value using the second-type labeling information.

The direct supervised learning implies supervised learning performed with respect to the voxels of the target region using the labeling information of the target region. The indirect supervised learning implies supervised learning performed with respect to the voxels of the target region using upper-layer structure labeling information of the target region. The weakly supervised learning implies learning performed when only some of the voxels of a single image have the labeling information assigned thereto and the other voxels do not have the labeling information assigned thereto.

In the following description of the embodiment, the explanation is given with reference to the lungs. However, for explanatory convenience, the terms “a tubular region”, “a massive region”, “a plurality of blocks” and “a plurality of categories corresponding to the concerned block” according to the scope of the claims are respectively referred to as “a trachea or a blood vessel”, “a lung region”, “a plurality of pulmonary lobes (i.e., pulmonary lobes of a plurality of categories corresponding to the lung region)”, and “a plurality of pulmonary sections corresponding to the pulmonary lobes”. Moreover, in the embodiment, tracheas and blood vessels are used as the structures that can be directly labeled. However, that is not the only possible case, and other structures can also be used. Furthermore, for example, a region that can be directly labeled can be considered as a “predetermined structure”.

FIG. 1 is a flowchart of the operations performed at the time of learning the segmentation model learning method according to the embodiment, and a usage flowchart of the operations performed at the time of segmentation using the already-learnt segmentation model.

As illustrated in FIG. 1, in the learning stage, firstly, at Step 100, the following information is obtained as learning data: three-dimensional medical image data; first-type labeling information meant for segmenting a tubular region into multiple segments (for example, a plurality of categories); second-type labeling information meant for segmenting a massive region, which covers the tubular region, into a plurality of blocks. The learning data is passed onto a segmentation model, and then the segmentation model outputs probability maps equal in number to the number of segmentation categories. In the embodiment, when the learning data is input thereto, the segmentation model outputs probability maps of 19 categories (in other words, outputs 19 channels) including probability maps of 18 categories (channels) corresponding to 18 pulmonary sections and a probability map of a single category (channel) corresponding to the background. In the probability map of each category, the voxel values represent the probability at which the concerned voxels belong to the corresponding category, and the voxel values are in the range of [0, 1]. The probability maps generated at Step 100 represent the probability maps of all voxels including the tubular region including tracheas and blood vessels, the lung region, and the background region.

FIG. 2 is a diagram illustrating an example of the first-type labeling information and the second-type labeling information according to the embodiment. The first-type labeling information is meant for segmenting the tubular region, such as tracheas and blood vessels, into multiple segments. As illustrated in FIG. 2, the tubular region is segmented into 18 pulmonary sections. For example, in the first-type labeling information, with respect to each of a plurality of voxels constituting the tubular region including tracheas and blood vessels, a label is assigned to indicate the pulmonary section, from among the 18 pulmonary sections, to which the concerned voxel belongs. The second-type labeling information is meant for segmenting the lung region into a plurality of pulmonary lobes. As illustrated in FIG. 2, the lung region is segmented into five pulmonary lobes. For example, in the second-type labeling information, with respect to each of a plurality of voxels constituting the lung region, a label is assigned to indicate the pulmonary lobe, from among the five pulmonary lobes, to which the concerned voxel belongs.

As the data to be used in learning, three-dimensional medical image data containing the lung region obtained as a result of tomography scanning is input to a segmentation model along with the first-type labeling information and the second-type labeling information; and then learning is performed.

Subsequently, at Step 200, depending on the region to which the voxels belong, a different supervised learning method is selected and supervised learning is performed. According to a conventional algorithm based on deep learning, it becomes possible to confirm (determine) whether the region to which the voxels belong is the background region, or the tubular region including tracheas and blood vessels, or the lung region. Then, for each region to which the voxels belong, the supervised learning method corresponding to that region is selected. That is, according to a conventional algorithm based on deep learning; the background region, the tubular region, and the lung region are segmented from the three-dimensional medical image data, and a learning method corresponding to each region is selected. Regarding Step 200, the detailed explanation is given later.

Subsequently, at Step 300, based on the loss function value (also referred to as the loss or the loss value) obtained at Step 200, various network parameters applied to the segmentation model are optimized so as to minimize the loss function value.

In the process of adjusting the network parameters of the segmentation model based on the loss function value, the operations from Step 100 to Step 300 need to be repeated using a large volume of sample data. After the regression accuracy is satisfied, the segmentation model becomes capable of directly outputting the lung region segmentation, the pulmonary lobe segmentation, and the pulmonary section segmentation based on medical image data (i.e., the medical image data that was input). At that time, the segmentation model is recognized to have been already learnt and outputs the already-learnt segmentation model (Step 400). For example, the already-learnt segmentation model performs segmentation according to a conventional algorithm based on deep learning of the two lungs (the region of the two lungs) and the tubular region (the region of tracheas and blood vessels) from the input medical image data. Then, the already-learnt segmentation model segments the two lungs into five pulmonary lobes (the regions of five pulmonary lobes), and segments the five pulmonary lobes into 18 pulmonary sections (the regions of 18 pulmonary sections). Moreover, the already-learnt segmentation model segments the tubular region into 18 pulmonary sections. Then, the already-learnt segmentation model outputs the segmentation result. It marks the end of the flow of the learning stage.

Meanwhile, in FIG. 1 is also illustrated the flowchart about the actual segmentation performed by the already-learnt segmentation model.

Firstly, at Step 500, three-dimensional medical image data to be segmented is obtained. Then, at Step 600, using the already-learnt segmentation model, segmentation is performed with respect to the three-dimensional medical image data to be segmented and the segmentation result is obtained. Based on the already-learnt segmentation model according to the embodiment, in the actual usage process, accurate segmentation can be completed without having to obtain the pulmonary section labeling of tracheas and blood vessels. Thus, as compared to the conventional technology, enhancement is achieved as far as the convenience is concerned.

Explained below with reference to FIGS. 3 to 6 is the supervised learning process performed at Step 200 according to the embodiment. In FIG. 3, the details given at Step 100, Step 300, and Step 400 are identical to the details given in FIG. 1. Hence, the same explanation is not given again. Thus, the following explanation is given only about Step 200.

The operation performed at Step 200 can be further divided into Step 201, Step 202, and Step 203.

At Step 201, the tubular region including tracheas and blood vessels has the first-type information assigned thereto as reference. Hence, regarding the voxels belonging to the tubular region including tracheas and blood vessels in each probability map, direct supervised learning is performed. Herein, the objective of the supervised learning is as follows. In a probability map of the pulmonary section category to which a voxel belongs, that voxel has the numerical value of "1". In the probability maps of other categories, that voxel has the numerical value of "0". With reference to a particular voxel in the pulmonary segment of the first right segment, the voxel desirably has the numerical value of "1" in the probability map representing the first right segment, but desirably has the numerical value of "0" in each probability map representing one of the second right segment, the third right segment, the fourth right segment, the fifth right segment, the sixth right segment, the seventh right segment, the eighth right segment, the ninth right segment, the 10-th right segment, the first left segment, the second left segment, the third left segment, the fourth left segment, the fifth left segment, the sixth left segment, the seventh left segment, the eighth left segment, and the background. Similarly, with reference to a particular voxel in the pulmonary segment of the second right segment, the voxel desirably has the numerical value of "1" in the probability map representing the second right segment, but desirably has the numerical value of "0" in each probability map representing one of the first right segment, the third right segment, the fourth right segment, the fifth right segment, the sixth right segment, the seventh right segment, the eighth right segment, the ninth right segment, the 10-th right segment, the first left segment, the second left segment, the third left segment, the fourth left segment, the fifth left segment, the sixth left segment, the seventh left segment, the eighth left segment, and the background.

Meanwhile, regarding the voxels belonging to the background too, direct supervised learning is performed. The objective of the supervised learning is as follows. In the probability map representing the background, the corresponding voxels have the numerical value of "1", and have the numerical value of "0" in the other 18 probability maps.

Figure 4:
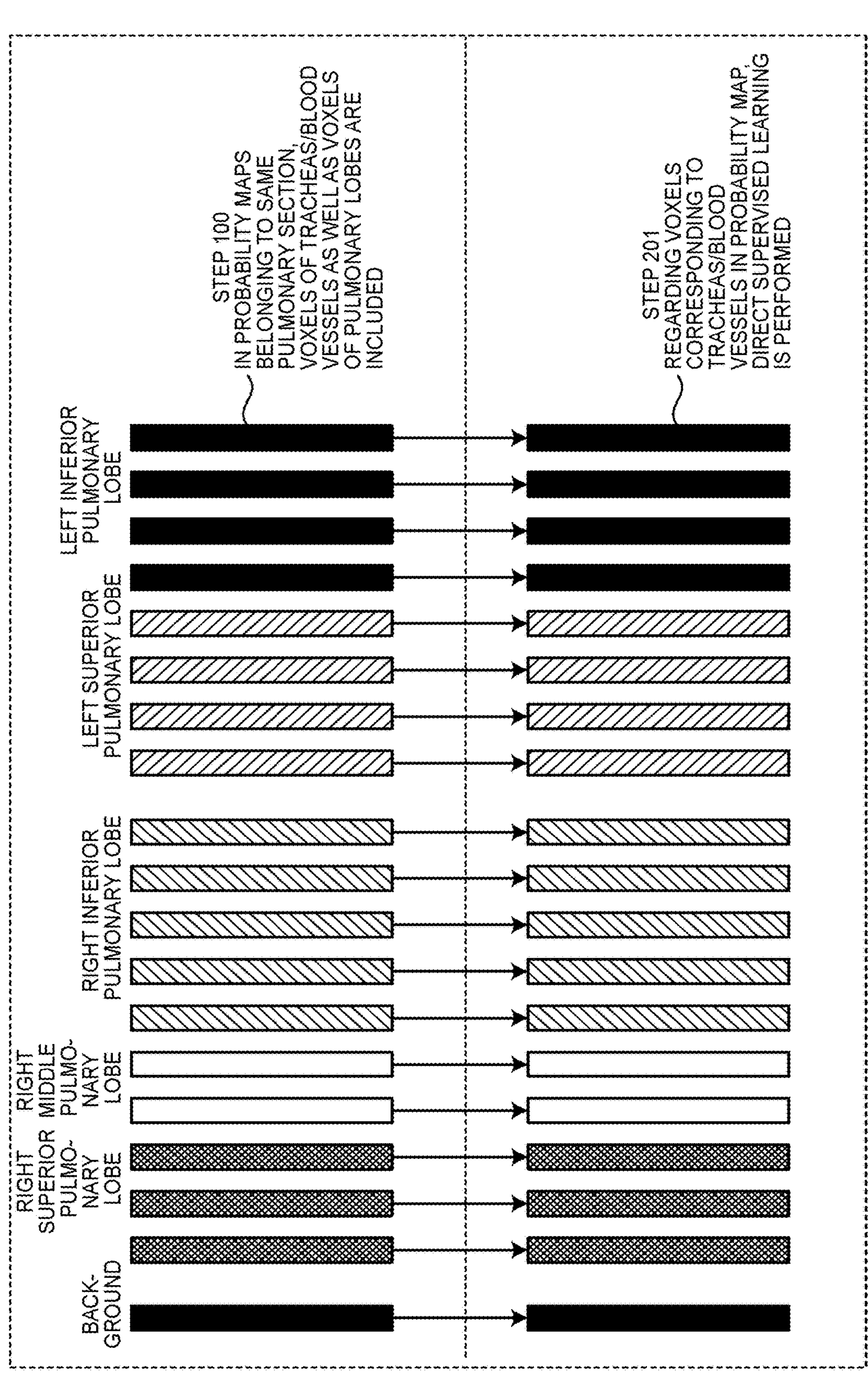
FIG. 4 is a schematic diagram illustrating an example of the relationship between a probability map generated at Step 100 and a probability map subjected to direct supervised learning at Step 201.

As illustrated in FIG. 4, at Step 100, the probability maps of 18 pulmonary sections and the probability map of a single background are generated. The probability map of each of the 18 pulmonary sections includes the voxels of the tracheas and the blood vessels belonging to the concerned pulmonary section, as well as includes the voxels of the pulmonary lobes belonging to the concerned pulmonary section. However, at Step 201, from among the probability map of the single background and the probability maps of the 18 pulmonary sections, direct supervised learning is performed using the voxels related to only the tracheas and the blood vessels.

In the direct supervised learning, the loss function value is calculated using Dice+CE, and the network parameters are adjusted based on the loss function value. Herein, using Dice+CE is mentioned only as an example. Alternatively, one or more of Dice, Cross Entropy, and Recall can be used in combination, and there is no particular restriction on the loss function.

At Step 202, indirect supervised learning is performed with respect to the voxels of the massive region representing a lung region. Herein, the objective of the supervised learning is as follows. Regarding a voxel, consider a case in which, in the probability maps of a plurality of categories corresponding to the block to which the voxel belongs (a plurality of pulmonary sections of the pulmonary lobe to which the voxel belongs), the voxel has the maximum numerical value of "1"; and consider a case in which, in the probability map of one of a plurality of categories corresponding to the block to which the voxel belongs (a single pulmonary section of the pulmonary lobe to which the voxel belongs), the voxel has the maximum numerical value of "1". In that case, in the probability maps of the other categories other than the concerned single category (i.e., in the probability maps of the other pulmonary sections other than the concerned single pulmonary section), the concerned voxel has the numerical value of "0". With reference to a particular voxel in the right superior pulmonary lobe, according to a conventional algorithm based on deep learning, although it can be identified (determined) that the voxel belongs to the right superior pulmonary lobe, it is not possible identify whether the voxel belongs to the first right segment, the second right segment, or the third right segment in the right superior pulmonary lobe. In that case, from the probability map of each of the first right segment, the second right segment, and the third right segment, a voxel corresponding to the concerned voxel can be extracted; the maximum numerical value from among the three extracted voxels can be treated as a voxel in a new probability map; and accordingly the probability maps of the right superior pulmonary lobe can be synthesized based on the probability map of each of the first right segment, the second right segment, and the third right segment.

Figure 5:
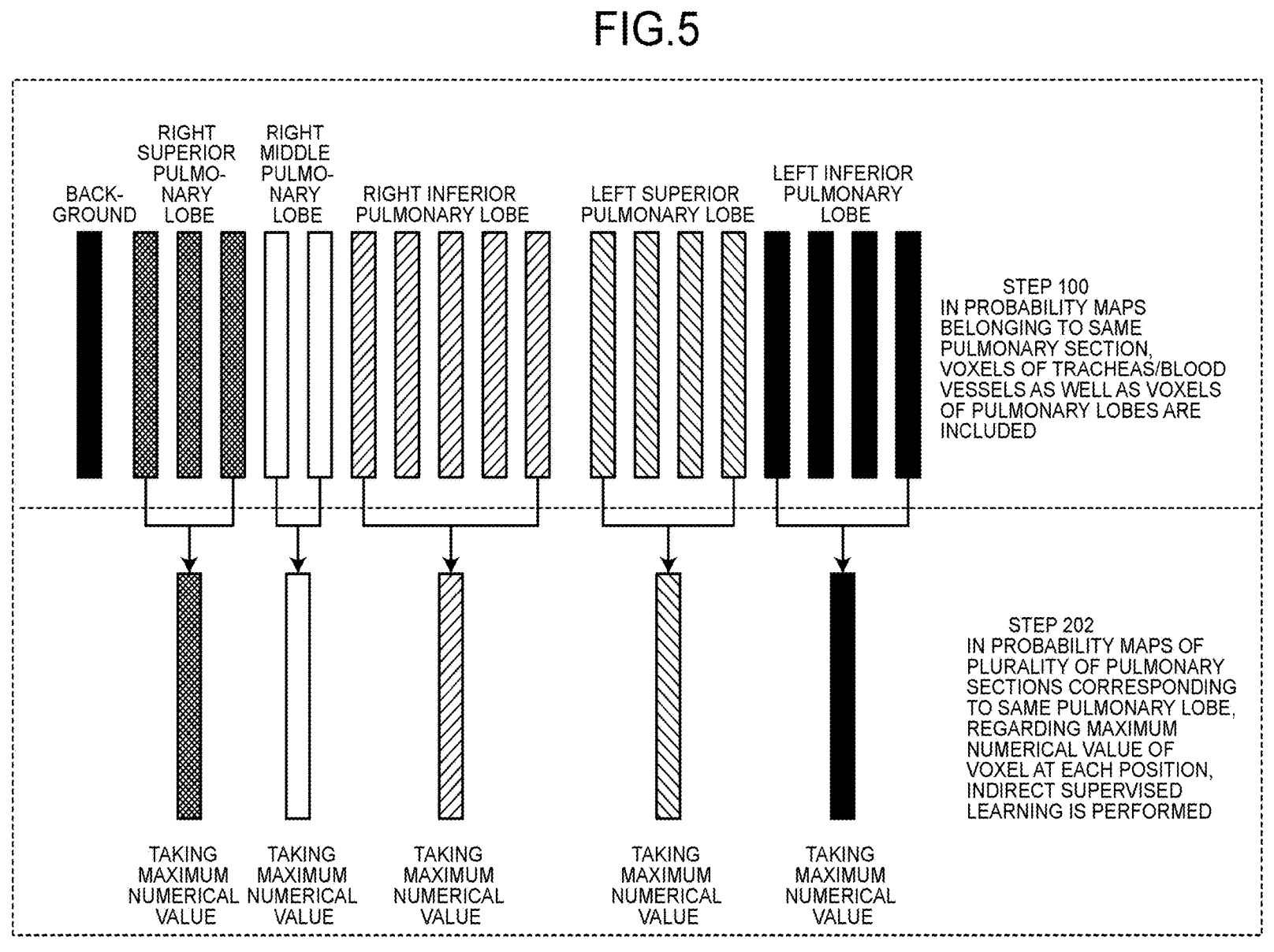

As illustrated in FIG. 5, at Step 100, the probability maps of 18 pulmonary sections are generated, as well as the probability map of a single background is generated. The probability map of each of the 18 pulmonary sections includes the voxels of the tracheas and the blood vessels belonging to the concerned pulmonary section as well as includes the voxels of the pulmonary lobes belonging to the concerned pulmonary section. At Step 202, regarding each pulmonary lobe, supervised learning is performed with respect to the voxels related to that pulmonary lobe using the second-type labeling information. Then, in order to achieve the objective mentioned above, for each pulmonary lobe, regarding each voxel in the probability maps of a plurality of pulmonary sections corresponding to the concerned pulmonary lobe, the maximum numerical value needs to be taken; and the probability maps need to be accordingly narrowed down from 18 pulmonary section categories (channels) to five pulmonary lobe categories (channels).

Figure 6:
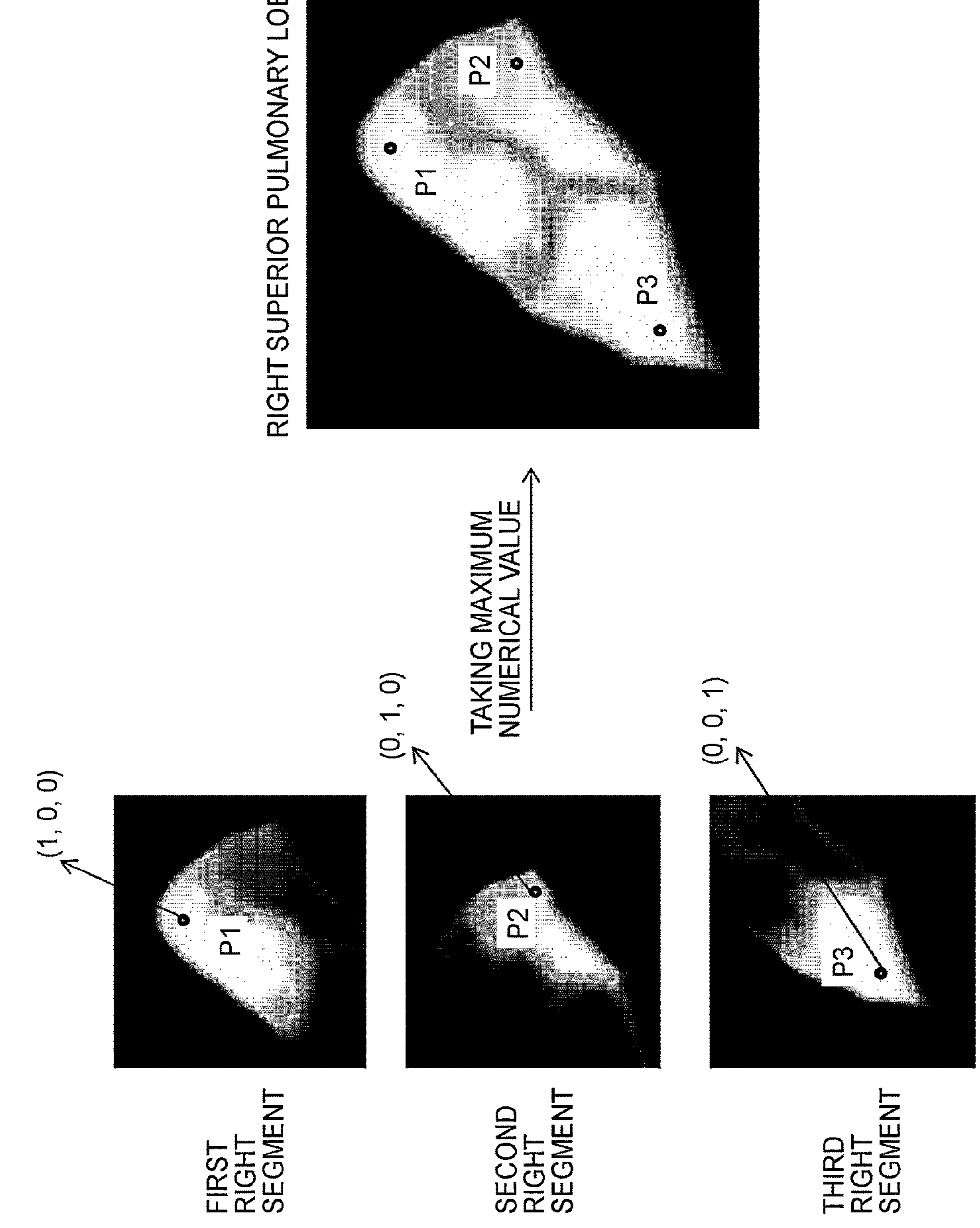
FIG. 6 is a diagram illustrating a probability map of the right superior pulmonary lobe obtained as a result taking the maximum numerical value from among the probability maps of a plurality of categories corresponding to the right superior pulmonary lobe.

In FIG. 6, as an example, a probability map of the right superior pulmonary lobe is illustrated that is obtained as a result taking the maximum numerical value from among the probability maps of three categories corresponding to the right superior pulmonary lobe. In FIG. 6, on the left side are illustrated the probability maps of three categories (channels) output at Step 100. The probability maps corresponding to the first right segment, the second right segment, and the third right segment represent the three pulmonary section categories belonging to the right superior pulmonary lobe.

In the indirect supervised learning, with respect to the probability maps of a plurality of categories corresponding to the block to which the concerned voxel belongs, supervised learning is performed in a simultaneous manner. In other words, in the indirect supervised learning, the second-type labeling information is used and supervised learning is performed with respect to the maximum numerical values in the probability maps of a plurality of categories. That is, the voxel corresponding to a voxel P1 illustrated in the first right segment in the medical image data has the numerical values of (1, 0, 0) as obtained in the probability maps of the first right segment, the second right segment, and the third right segment. Moreover, the voxel corresponding to a voxel P2 illustrated in the second right segment in the medical image data has the numerical values of (0, 1, 0) as obtained in the probability maps of the first right segment, the second right segment, and the third right segment. Furthermore, the voxel corresponding to a voxel P3 illustrated in the third right segment in the medical image data has the numerical values of (0, 0, 1) as obtained in the probability maps of the first right segment, the second right segment, and the third right segment. Accordingly, regarding the voxel P1, the voxel having the maximum numerical value in the first right segment is treated as the voxel in the new probability map of the right superior pulmonary lobe. Moreover, regarding the voxel P2, the voxel having the maximum numerical value in the second right segment is treated as the voxel in the new probability map of the right superior pulmonary lobe. Furthermore, regarding the voxel P3, the voxel having the maximum numerical value in the third right segment is treated as the voxel in the new probability map of the right superior pulmonary lobe. Meanwhile, although it is desirable to have the maximum numerical value equal to "1", there is a possibility that the maximum numerical value falls short of "1" in the actual learning. Thus, at the time of selection, the maximum numerical value from among the probability maps of a plurality of categories can be selected. Regarding the other voxels too, in an identical manner, the maximum numerical values from among three probability maps are taken, and probability maps corresponding to the right superior pulmonary lobe are generated. Then, based on the probability maps of the right superior pulmonary lobe and the second-type labeling information, the loss function value is calculated using Dice+CE, and the network parameters are adjusted based on the loss function value. Herein, using Dice+CE is mentioned only as an example. Alternatively, one or more of Dice, Cross Entropy, and Recall can be used in combination, and there is no particular restriction on the loss function.

Meanwhile, during the execution of the operations at Step 201 and Step 202, the operation at Step 203 is also performed. At Step 203, regarding the labeling consistency of the proximal voxels (including adjacent voxels), supervised learning is performed. Herein, it is desirable that the proximal voxels have identical labeling assigned thereto. As a result of assigning identical labeling to the proximal voxels as much as possible, it becomes possible to hold down serration at the boundaries among the segments, and to obtain smooth boundaries. As far as the means of achieving labeling consistency is concerned, there is no particular restriction on the objective function used at Step 203, and a loss function L1 of a probability map can be Laplacian.

That is, the following holds true.

$$\mathrm{Loss}_{L1} := \|\nabla(\text{probability map})\|_1$$

$$\mathrm{Loss}_{Laplacian} := \|\Delta(\text{probability map})\|_1 = \|\nabla\cdot\nabla(\text{probability map})\|_1$$

Herein, "probability map" represents a probability map generated at Step 100; "$\|\nabla(\text{probability map})\|_1$" indicates obtaining the gradients of the probability maps generated at Step 100 and adding the gradients; "$\|\Delta(\text{probability map})\|_1$" indicates obtaining the Laplacian of the probability maps generated at Step 100 and adding the Laplacian; and "$\|\nabla\cdot\nabla(\text{probability map})\|_1$" indicates obtaining the dispersion slopes of the probability maps generated at Step 100 and adding the dispersion slopes. It is believed that, smaller the loss function value calculated according to the loss function mentioned above, the higher is the labeling consistency of the proximal voxels. At Step 203, the network parameters are adjusted in such a way that the loss function value becomes smaller.

Figure 7:
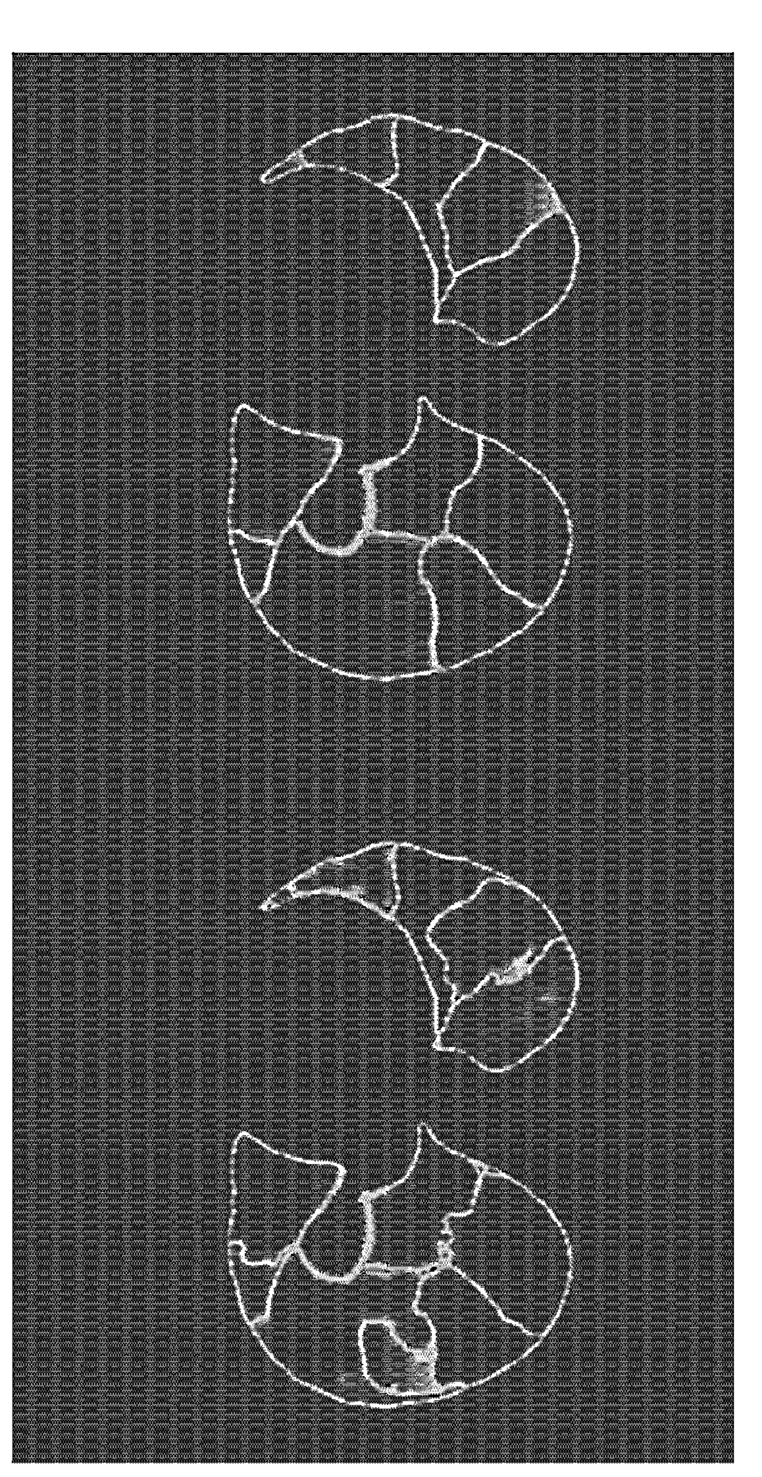
FIG. 7 is a diagram illustrating a probability map before the learning of the labeling consistency and illustrating a probability map after the learning of the labeling consistency.

FIG. 7 is a diagram illustrating a probability map before the learning of the labeling consistency and illustrating a probability map after the learning of the labeling consistency. As can be understood from FIG. 7, as a result of performing supervised learning of the labeling consistency, it becomes possible to obtain the segmentation result having smooth boundaries.

After learning is performed from Step 100 to Step 400, an already-learnt segmentation model is obtained. To the already-learnt segmentation model, when the three-dimensional medical image data to be segmented is input, it becomes possible to obtain an excellent segmentation result having different display formats as illustrated in FIG. 8. For example, as illustrated on the left side in FIG. 8, a segmentation result can be obtained in which five pulmonary lobes are segmented into 18 pulmonary sections. Moreover, for example, as illustrated on the right side in FIG. 8, a segmentation result can be obtained in which the tubular region is segmented into 18 pulmonary sections.

Other Embodiments

At Step 202 explained above, the explanation is given about an example in which the maximum numerical values in the probability maps of a plurality of categories are obtained for each pulmonary lobe. However, in some special cases, the fissures among the pulmonary lobes are not clearly distinguishable, and the pulmonary lobes cannot be segmented. In such a case, labeling can be performed based on the left lung and the right lung; the second-type labeling information meant for segmenting the lung region into two blocks can be obtained; the maximum numerical values can be obtained from the probability maps of a plurality of categories corresponding to the left lung and the right lung; supervised learning can be performed with respect to the maximum numerical values using the second-type labeling information; and the network parameters can be optimized.

Meanwhile, the massive region can be a pulmonary lobe.

Moreover, the indirect supervised learning according to the embodiment can be implemented also with respect to the hepatic lobe and the liver in the liver region. In that case, the hepatic lobe or the liver represents the massive region.

In the embodiment described above, the explanation is given about a segmentation model learning method. Herein, the understanding is that, as long as the various functions in the segmentation model learning method are implementable, the functions can be implemented using hardware or can be implemented using a combination of hardware and software.

For example, when the segmentation model learning method is implemented using a processor representing processing circuitry, the processing functions of the processor are stored as computer-executable programs in a memory circuit. The processor reads the computer programs from the memory circuit and executes them to implement the functions corresponding to the computer programs. Alternatively, instead of storing the computer programs in a memory circuit, the computer programs can be directly embedded into the circuit of the processor. In that case, the processor reads the computer programs, which are embedded in the circuit, and executes them to implement the functions. Meanwhile, the processor according to the embodiment described above is not limited to be configured as a single circuit. Alternatively, a plurality of independent circuits can be combined to configure as a single processor, and the functions thereof can be implemented.

Figure 9:
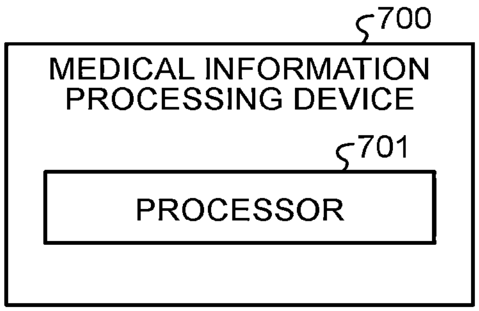
FIG. 9 is a diagram illustrating an example of a medical information processing device according to the embodiment.

The processor described above can be included in, for example, a medical information processing device such as a server. For example, as illustrated in FIG. 9, a medical information processing device 700 such as a server may include the processor 701 described above.

In the explanation given above, the term "processor" implies circuitry such as a central processing unit (CPU), a graphics processing unit (GPU), an application specific integrated circuit (ASIC), or a programmable logic apparatus (for example, a simple programmable logic apparatus (SPLD), a complex programmable logic apparatus (CPLD), or a field programmable gate array (FPGA)).

The computer programs executed by the processor can be stored in advance in a read only memory (ROM) or a memory circuit. Alternatively, the computer programs can be recorded as installable files or executable files in a computer-readable memory medium such as a compact disc read only memory (CD-ROM), a flexible disk (FD), a compact disc recordable (CD-R), or a digital versatile disc (DVD).

Still alternatively, the computer programs can be stored in a downloadable manner in a computer connected to a network such as the Internet.

Meanwhile, instead of implementing the segmentation model learning method, an already-learnt segmentation model can be stored in a server or in a computer connected to a network such as the Internet, so that another medical information processing device can download the already-learnt segmentation model via the network and use it. The other medical information processing device can call the already-learnt segmentation model and implement the segmentation result. For example, the other medical information processing device includes an input unit (an obtaining unit) that obtains the target medical image data for segmentation which is collected from the examination target, and that obtains an already-learnt segmentation model; a processing unit that uses the already-learnt segmentation model and segments the target medical image data for segmentation, and obtains the segmentation result indicating the segmentation of a tubular region and a massive region, which covers the tubular region, into multiple segments (for example, 18 pulmonary segments); and an output unit that outputs the segmentation result. Herein, the output unit is, for example, a display used to display the segmentation result.

According to at least one embodiment described above, without having to use the total pulmonary segment labeling, it becomes possible to enhance the learning efficiency, and to avoid a decline in the accuracy attributed to the difficulty or the differences in the total labeling. Moreover, at the time of actually performing the segmentation using an already-learnt segmentation model, the segmentation can be performed without having to generate pulmonary section labeling, and comparatively smoother segmentation boundaries can be obtained.

According to at least one embodiment described above, it becomes possible to enhance the efficiency and the accuracy of the learning process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A segmentation model learning method based on weakly supervised learning, comprising:
obtaining, as learning data,
medical image data,
first-type labeling information meant for segmenting a predetermined structure into a plurality of categories, and
second-type labeling information meant for segmenting a massive region, which covers the predetermined structure, into a plurality of blocks; and
learning that, based on a loss function value, includes performing supervised learning of voxel in the medical image data according to a region to which the voxel belongs, wherein
the learning of the medical image data includes
using the first-type labeling information about voxel of the predetermined structure and causing a segmentation model to perform direct supervised learning that represents learning for segmentation of the predetermined structure in target medical image data for segmentation into a plurality of categories,
using the second-type labeling information about voxel of the massive region and causing the segmentation model to perform indirect supervised learning that represents learning for segmentation of the massive region in the target medical image data for segmentation into a plurality of categories, and
optimizing network parameter of the segmentation model.

2. The segmentation model learning method according to claim 1, wherein, the indirect supervised learning in the learning includes
obtaining, regarding each voxel of the massive region, maximum numerical value from among numerical values of concerned voxel in probability maps of a plurality of categories corresponding to a block to which concerned voxel belongs, and
performing supervised learning using the second-type labeling information regarding the maximum numerical value.

3. The segmentation model learning method according to claim 2, wherein, in the indirect supervised learning, when the maximum numerical value is equal to “1” and when maximum numerical value in a probability map of a single category from among a plurality of categories corresponding to a block to which concerned voxel belongs is equal to “1”, supervised learning is performed in such a way that numerical value of concerned voxel becomes equal to “0” in a probability map of other category other than the single category.

4. The segmentation model learning method according to claim 1, wherein the learning further includes learning labeling consistency of proximal voxels in such a way that the proximal voxels have identical labeling.

5. The segmentation model learning method according to claim 1, wherein the predetermined structure is a tubular region.

6. The segmentation model learning method according to claim 5, wherein the tubular region is a blood vessel or a trachea.

7. The segmentation model learning method according to claim 5, wherein the massive region is either one of a lung, a pulmonary lobe, liver, and hepatic lobe.

8. A medical information processing device comprising:
an obtaining unit that obtains
target medial image data for segmentation which is collected from an examination target, and
an already-learnt segmentation model;
a processing unit that
segments the target medical image data for segmentation using the already-learnt segmentation model, and
obtains a segmentation result indicating segmentation of a predetermined structure and a massive region, which covers the predetermined structure, into a plurality of categories; and
an output unit that outputs the segmentation result, wherein
the already-learnt segmentation model is a segmentation model learnt according to the segmentation model learning method according to claim 1.

9. Processing circuitry that
obtains, as learning data,
medical image data,
first-type labeling information meant for segmenting a predetermined structure into a plurality of categories, and
second-type labeling information meant for segmenting a massive region, which covers the predetermined structure, into a plurality of blocks; and
performs learning that, based on a loss function value, includes
performing supervised learning of voxel in the medical image data according to a region to which the voxel belongs and by
using the first-type labeling information about voxel of the predetermined structure and causing a segmentation model to perform direct supervised learning that represents learning for segmentation of the predetermined structure in target medical image data for segmentation into a plurality of categories, and
using the second-type labeling information about voxel of the massive region and causing the segmentation model to perform indirect supervised learning that represents learning for segmentation of the massive region in the target medical image data for segmentation into a plurality of categories, and
optimizing network parameter of the segmentation model.

10. A computer program product having a non-transitory computer-readable medium including programmed instructions, wherein the instructions, when executed by a computer, cause the computer to perform:
obtaining, as learning data,
medical image data,
first-type labeling information meant for segmenting a predetermined structure into a plurality of categories, and
second-type labeling information meant for segmenting a massive region, which covers the predetermined structure, into a plurality of blocks; and
learning that, based on a loss function value, includes performing supervised learning of voxel in the medical image data according to a region to which the voxel belongs, wherein the supervised learning of the medical image data includes using the first-type labeling information about voxel of the predetermined structure and causing a segmentation model to perform direct supervised learning that represents learning for segmentation of the predetermined structure in target medical image data for segmentation into a plurality of categories, using the second-type labeling information about voxel of the massive region and causing the segmentation model to perform indirect supervised learning that represents learning for segmentation of the massive region in the target medical image data for segmentation into a plurality of categories, and optimizing network parameter of the segmentation model.

* * * * *